United States Patent
Taubert et al.

(10) Patent No.: US 12,044,682 B2
(45) Date of Patent: Jul. 23, 2024

(54) METHOD AND MEANS FOR DIAGNOSING AUTOIMMUNE HEPATITIS USING AUTOANTIBODY MARKERS

(71) Applicant: MEDIZINISCHE HOCHSCHULE HANNOVER, Hannover (DE)

(72) Inventors: Richard Taubert, Hannover (DE); Elmar Jaeckel, Hannover (DE); Niklas T. Baerlecken, Cologne (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 1056 days.

(21) Appl. No.: 16/754,006

(22) PCT Filed: Oct. 26, 2018

(86) PCT No.: PCT/EP2018/079369
§ 371 (c)(1),
(2) Date: Apr. 6, 2020

(87) PCT Pub. No.: WO2019/081692
PCT Pub. Date: May 2, 2019

(65) Prior Publication Data
US 2020/0264178 A1 Aug. 20, 2020

(30) Foreign Application Priority Data
Oct. 27, 2017 (EP) .................... 17198912

(51) Int. Cl.
| G01N 33/543 | (2006.01) |
| A61B 5/00 | (2006.01) |
| G01N 33/564 | (2006.01) |
| G01N 33/576 | (2006.01) |
| A61K 31/52 | (2006.01) |
| A61K 31/573 | (2006.01) |

(52) U.S. Cl.
CPC .......... *G01N 33/5767* (2013.01); *A61B 5/41* (2013.01); *G01N 33/564* (2013.01); *A61K 31/52* (2013.01); *A61K 31/573* (2013.01); *G01N 2800/52* (2013.01)

(58) Field of Classification Search
None
See application file for complete search history.

(56) References Cited

U.S. PATENT DOCUMENTS

| 5,830,667 A | 11/1998 | Alvarez | |
| 7,790,384 B2 * | 9/2010 | Ross ............ | C07K 16/30 435/6.14 |
| 2003/0232392 A1 | 12/2003 | Lohse | |

FOREIGN PATENT DOCUMENTS

WO     1998/035987 A1    8/1998

OTHER PUBLICATIONS

Bradley et al., Serum antibodies to Huntingtin Interacting Protein-1: A new blood test for Prostate Cancer, Cancer Res 2005; 65; (10), pp. 4126-4133, (Year: 2005).*
Torzewski et al., Animal Models of C-Reactive Protein, Hindawl Publishing Corporation, Mediators of Inflammation, vol. 2014, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Corrigan et al., Autoimmune hepatitis: an approach to disease understanding and management, British Medical Bulletin, 2015, 114, pp. 181-191. (Year: 2015).*
Strongin, Laboratory Diagnosis of Viral Infections, Sensitivity, Specificity, and Predictive Value of Diagnostic Tests: Definitions and Clinical Applications, Lennette, ed. Marcel Dekker, Inc. New York, pp. 211-219, 1992. (Year: 1992).*
Hausdorf et al: "Autoantibodies to asialoglycoprotein receptro (ASGPR) measured by a novel ELISA-Revival of a disease-activity marker in autoimmune hepatitis", Clinica Chimica Acta, vol. 408, No. 1-2, pp. 19-24, Oct. 1, 2009.
Scanlan et al: "Cancer-related serological recognition of human colon cancer: Identification of potential diagnositc and immunotherapeutic targets", Cancer Research, AACR—American Association for Cancer Research, vol. 62, No. 14, pp. 4041-4047, Jul. 15, 2002.

* cited by examiner

*Primary Examiner* — Gary Counts
(74) *Attorney, Agent, or Firm* — WC&F IP

(57) ABSTRACT

A method for determining or diagnosing the presence or absence, or the risk of development, or the therapy control of autoimmune hepatitis in a subject is provided. In a method, the presence or absence of antibodies against the huntingtin interacting protein 1 related protein (HIP1R) or against immunoreactive peptides derived therefrom are analyzed, the presence of said antibodies is indicative for the presence, or the risk of development or for therapy control of autoimmune hepatitis of the subject. The use of the HIP1R or an immunoreactive peptide derived therefrom in the diagnosis, the risk assessment or therapy control of hepatitis diseases by determining the presence of antibodies against said HIP1R or immunoreactive peptide derived therefrom, may be helpful for differential diagnosis of autoimmune hepatitis.

10 Claims, 3 Drawing Sheets
Specification includes a Sequence Listing.

SEQUENCE LISTING

<160> NUMBER OF SEQ ID NOS: 2

<210> SEQ ID NO 1
<211> LENGTH: 1068
<212> TYPE: PRT
<213> ORGANISM: homo sapiens

<400> SEQUENCE: 1

```
Met Asn Ser Ile Lys Asn Val Pro Ala Arg Val Leu Ser Arg Arg Pro
1               5                   10                  15

Gly His Ser Leu Glu Ala Glu Arg Glu Gln Phe Asp Lys Thr Gln Ala
            20                  25                  30

Ile Ser Ile Ser Lys Ala Ile Asn Thr Gln Glu Ala Pro Val Lys Glu
        35                  40                  45

Lys His Ala Arg Arg Ile Ile Leu Gly Thr His His Glu Lys Gly Ala
    50                  55                  60

Phe Thr Phe Trp Ser Tyr Ala Ile Gly Leu Pro Leu Pro Ser Ser Ser
65                  70                  75                  80

Ile Leu Ser Trp Lys Phe Cys His Val Leu Lys Val Leu Arg Asp
                85                  90                  95

Gly His Pro Asn Val Leu His Asp Cys Gln Arg Tyr Arg Ser Asn Ile
            100                 105                 110

Arg Glu Ile Gly Asp Leu Trp Gly His Leu His Asp Arg Tyr Gly Gln
        115                 120                 125

Leu Val Asn Val Tyr Thr Lys Leu Leu Leu Thr Lys Ile Ser Phe His
    130                 135                 140

Leu Lys His Pro Gln Phe Pro Ala Gly Leu Glu Val Thr Asp Glu Val
145                 150                 155                 160

Leu Glu Lys Ala Ala Gly Thr Asp Val Asn Asn Ile Phe Gln Leu Thr
                165                 170                 175

Val Glu Met Phe Asp Tyr Met Asp Cys Glu Leu Lys Leu Ser Glu Ser
            180                 185                 190

Val Phe Arg Gln Leu Asn Thr Ala Ile Ala Val Ser Gln Met Ser Ser
        195                 200                 205

Gly Gln Cys Arg Leu Ala Pro Leu Ile Gln Val Ile Gln Asp Cys Ser
    210                 215                 220

His Leu Tyr His Tyr Thr Val Lys Leu Leu Phe Lys Leu His Ser Cys
225                 230                 235                 240

Leu Pro Ala Asp Thr Leu Gln Gly His Arg Asp Arg Phe His Glu Gln
                245                 250                 255

Phe His Ser Leu Arg Asn Phe Phe Arg Arg Ala Ser Asp Met Leu Tyr
            260                 265                 270

Phe Lys Arg Leu Ile Gln Ile Pro Arg Leu Pro Glu Gly Pro Pro Asn
        275                 280                 285

Phe Leu Arg Ala Ser Ala Leu Ala Glu His Ile Lys Pro Val Val Val
    290                 295                 300

Ile Pro Glu Glu Ala Pro Glu Asp Glu Pro Glu Asn Leu Ile Glu
305                 310                 315                 320

Ile Ser Thr Gly Pro Pro Ala Gly Glu Pro Val Val Val Ala Asp Leu
                325                 330                 335

Phe Asp Gln Thr Phe Gly Pro Pro Asn Gly Ser Val Lys Asp Asp Arg
            340                 345                 350

Asp Leu Gln Ile Glu Ser Leu Lys Arg Glu Val Glu Met Leu Arg Ser
        355                 360                 365
```

-continued

```
Glu Leu Glu Lys Ile Lys Leu Glu Ala Gln Arg Tyr Ile Ala Gln Leu
370                 375                 380
Lys Ser Gln Val Asn Ala Leu Glu Gly Glu Leu Glu Glu Gln Arg Lys
385                 390                 395                 400
Gln Lys Gln Lys Ala Leu Val Asp Asn Glu Gln Leu Arg His Glu Leu
            405                 410                 415
Ala Gln Leu Arg Ala Ala Gln Leu Glu Gly Glu Arg Ser Gln Gly Leu
        420                 425                 430
Arg Glu Glu Ala Glu Arg Lys Ala Ser Ala Thr Glu Ala Arg Tyr Asn
    435                 440                 445
Lys Leu Lys Glu Lys His Ser Glu Leu Val His Val His Ala Glu Leu
450                 455                 460
Leu Arg Lys Asn Ala Asp Thr Ala Lys Gln Leu Thr Val Thr Gln Gln
465                 470                 475                 480
Ser Gln Glu Glu Val Ala Arg Val Lys Glu Gln Leu Ala Phe Gln Val
            485                 490                 495
Glu Gln Val Lys Arg Glu Ser Glu Leu Lys Leu Glu Glu Lys Ser Asp
        500                 505                 510
Gln Leu Glu Lys Leu Lys Arg Glu Leu Glu Ala Lys Ala Gly Glu Leu
    515                 520                 525
Ala Arg Ala Gln Glu Ala Leu Ser His Thr Glu Gln Ser Lys Ser Glu
530                 535                 540
Leu Ser Ser Arg Leu Asp Thr Leu Ser Ala Glu Lys Asp Ala Leu Ser
545                 550                 555                 560
Gly Ala Val Arg Gln Arg Glu Ala Asp Leu Leu Ala Ala Gln Ser Leu
            565                 570                 575
Val Arg Glu Thr Glu Ala Ala Leu Ser Arg Glu Gln Gln Arg Ser Ser
        580                 585                 590
Gln Glu Gln Gly Glu Leu Gln Gly Arg Leu Ala Glu Arg Glu Ser Gln
    595                 600                 605
Glu Gln Gly Leu Arg Gln Arg Leu Leu Asp Glu Gln Phe Ala Val Leu
610                 615                 620
Arg Gly Ala Ala Ala Glu Ala Ala Gly Ile Leu Gln Asp Ala Val Ser
625                 630                 635                 640
Lys Leu Asp Asp Pro Leu His Leu Arg Cys Thr Ser Ser Pro Asp Tyr
            645                 650                 655
Leu Val Ser Arg Ala Gln Glu Ala Leu Asp Ala Val Ser Thr Leu Glu
        660                 665                 670
Glu Gly His Ala Gln Tyr Leu Thr Ser Leu Ala Asp Ala Ser Ala Leu
    675                 680                 685
Val Ala Ala Leu Thr Arg Phe Ser His Leu Ala Ala Asp Thr Ile Ile
690                 695                 700
Asn Gly Gly Ala Thr Ser His Leu Ala Pro Thr Asp Pro Ala Asp Arg
705                 710                 715                 720
Leu Ile Asp Thr Cys Arg Glu Cys Gly Ala Arg Ala Leu Glu Leu Met
            725                 730                 735
Gly Gln Leu Gln Asp Gln Gln Ala Leu Arg His Met Gln Ala Ser Leu
        740                 745                 750
Val Arg Thr Pro Leu Gln Gly Ile Leu Gln Leu Gly Gln Glu Leu Lys
    755                 760                 765
Pro Lys Ser Leu Asp Val Arg Gln Glu Glu Leu Gly Ala Val Val Asp
770                 775                 780
Lys Glu Met Ala Ala Thr Ser Ala Ala Ile Glu Asp Ala Val Arg Arg
```

```
            785                 790                 795                 800

Ile Glu Asp Met Met Asn Gln Ala Arg His Ala Ser Ser Gly Val Lys
                        805                 810                 815

Leu Glu Val Asn Glu Arg Ile Leu Asn Ser Cys Thr Asp Leu Met Lys
                        820                 825                 830

Ala Ile Arg Leu Leu Val Thr Thr Ser Thr Ser Leu Gln Lys Glu Ile
                        835                 840                 845

Val Glu Ser Gly Arg Gly Ala Ala Thr Gln Gln Glu Phe Tyr Ala Lys
                    850                 855                 860

Asn Ser Arg Trp Thr Glu Gly Leu Ile Ser Ala Ser Lys Ala Val Gly
        865                 870                 875                 880

Trp Gly Ala Thr Gln Leu Val Glu Ala Ala Asp Lys Val Val Leu His
                        885                 890                 895

Thr Gly Lys Tyr Glu Glu Leu Ile Val Cys Ser His Glu Ile Ala Ala
                        900                 905                 910

Ser Thr Ala Gln Leu Val Ala Ala Ser Lys Val Lys Ala Asn Lys His
                        915                 920                 925

Ser Pro His Leu Ser Arg Leu Gln Glu Cys Ser Arg Thr Val Asn Glu
                    930                 935                 940

Arg Ala Ala Asn Val Val Ala Ser Thr Lys Ser Gly Gln Glu Gln Ile
        945                 950                 955                 960

Glu Asp Arg Asp Thr Met Asp Phe Ser Gly Leu Ser Leu Ile Lys Leu
                        965                 970                 975

Lys Lys Gln Glu Met Glu Thr Gln Val Arg Val Leu Glu Leu Glu Lys
                        980                 985                 990

Thr Leu Glu Ala Glu Arg Met Arg  Leu Gly Glu Leu Arg Lys Gln His
                    995                 1000                1005

Tyr Val  Leu Ala Gly Ala Ser  Gly Ser Pro Gly Glu  Glu Val Ala
                    1010                1015                1020

Ile Arg  Pro Ser Thr Ala Pro  Arg Ser Val Thr Thr  Lys Lys Pro
                    1025                1030                1035

Pro Leu  Ala Gln Lys Pro Ser  Val Ala Pro Arg Gln  Asp His Gln
                    1040                1045                1050

Leu Asp  Lys Lys Asp Gly Ile  Tyr Pro Ala Gln Leu  Val Asn Tyr
                    1055                1060                1065

<210> SEQ ID NO 2
<211> LENGTH: 42
<212> TYPE: PRT
<213> ORGANISM: homo sapiens

<400> SEQUENCE: 2

Met Gly Gln Leu Gln Asp Gln Gln Ala Leu Arg His Met Gln Ala Ser
1               5                   10                  15

Leu Val Arg Thr Pro Leu Gln Gly Ile Leu Gln Leu Gly Gln Glu Leu
                20                  25                  30

Lys Pro Lys Ser Leu Asp Val Arg Gln Glu
            35                  40
```

METHOD AND MEANS FOR DIAGNOSING AUTOIMMUNE HEPATITIS USING AUTOANTIBODY MARKERS

The present invention relates generally to a method for determining or diagnosing the presence or absence, or the risk of development, or the therapy control of autoimmune hepatitis in a subject, in particular, in mammals. In addition, the present invention relates to test kits for use in the diagnosis or the determination of the presence or absence, or the risk of development or the therapy control of autoimmune hepatitis in a subject. In particular, the present invention relates to a method wherein the presence or absence of antibodies against the huntingtin interacting protein 1 related protein (HIP1R) or against immunoreactive peptides derived therefrom are analyzed, the presence of said antibodies is indicative for the presence, or the risk of development or for therapy control of autoimmune hepatitis of said subject. Further, the present invention relates to the use of the HIP1R or an immunoreactive peptide derived therefrom in the diagnosis, the risk assessment or therapy control of hepatitis diseases by determining the presence of antibodies, in particular, autoantibodies against said HIP1R or immunoreactive peptide derived therefrom, this is particularly helpful for differential diagnosis of autoimmune hepatitis.

BACKGROUND OF THE INVENTION

Autoimmune hepatitis (AIH) accounts for 5 to 10% of chronic hepatitis and manifests in all age groups. It is formerly also known as lupoid hepatitis, representing a chronic autoimmune disease of the liver that occurs when the body's immune system attacks liver cells causing liver to be inflamed. Common initial symptoms include fatigue, joint or muscle aches or signs of acute liver inflammation including fever, jaundice, and right upper quadrant abdominal pain. Unfortunately, individuals with autoimmune hepatitis often have no initial symptoms and the disease is detected by abnormal liver function tests only.

That is, an abnormal immune response due to a cell mediated immune response against the body's own liver results in inflammation of the liver, which can lead to further symptoms or complications such as liver fibrosis and, eventually, cirrhosis.

On the one hand, autoimmune hepatitis may be present completely asymptotic with signs of chronic liver disease, acute or even fulminant hepatic failure. On the other hand, subjects suffering from AIH present with one or more non-specific symptoms or may have only laboratory abnormalities at their initial presentation but also the subject may already developed cirrhosis at the time point of diagnosis. Further, it has been noted that autoimmune hepatitis frequently appears associated with other autoimmune conditions like celiac disease, vasculitis and autoimmune thyroiditis.

Currently there are no specific or pathognomonic criteria to diagnose an AIH. That means, all other and more likely causes for a hepatitis have to be excluded which means that diagnosis is only indirectly possible excluding other hepatic diseases like chronic viral infections, (non-alcoholic) fatty liver disease, metabolic liver disease, alcohol, drugs, vascular, cholestatic liver diseases etc. Thus, diagnosis and determination of AIH represents a challenging task for laboratory diagnosis. One reason is that there is no direct test to diagnose AIH, rather, be diagnosed by differential diagnosis excluding other disease with similar symptoms, as mentioned before (Manns et al. Hepatology. 2010 June; 51(6):2193-213)).

The most relevant tool to screen for an AIH is the analysis of a set of autoantibodies, namely, anti-nuclear antibodies (ANA), anti-smooth muscle antibody (SMA), and liver kidney microsomal antibody (LKM) in patients' blood. These three antibody types are found in about 80 to 90% of AIH patients and are tested in various dilution steps with an indirect immunofluorescence staining on rodent tissue sections of liver, kidney and stomach. However, at present the diagnosis of autoimmune hepatitis always requires a liver biopsy.

Further, the autoantibodies mentioned above, namely, ANA, SMA and LKM are also detectable in other liver diseases, thus, techniques allowing to detect ANA, SMA and LKM lack sufficient sensitivities and specificities and are inferior due to the immunofluorescence approach. Namely, the tissue sections staining with the autoantibodies have to be analyzed under a fluorescent microscope and the staining pattern have to be evaluated in terms of staining intensity and staining pattern (anatomical region of positive staining, etc.) by an experienced technician. Thus, there is still the recommendation to obtain a liver biopsy for further diagnosis.

In a meta-analysis, sensitivities and specificities of ANA (about 65% and 75.1%) and SMA (about 50.3% and 92.6%) were moderate to low. Anti-SLA (anti-soluble liver antigen) is a more AIH specific (98.9%) antibody but with a low sensitivity (19.4%), see Zhang et al, PLOS 1, 2014, 9, e92267. LKM is only detectable in the rare AIH type 2.

Presently, four subtypes of AIH are recognized:
1. positive ANA and SMA with elevated immunoglobulin G (classic form, responds well to low dose steroids), this is the most common type of disease. It can develop at any age. Up to half the people with type 1 autoimmune hepatitis have other autoimmune disorders, such as celiac disease or rheumatoid arthritis;
2. positive LKM-1, LKM-2 or LKM-3 whereby typically female children and teenager are affected by this type 2 of AIH;
3. Positive antibodies against soluble liver antigen. This group is typically included into group 1) having anti-SLA or anti-LP (liver-pancreas) autoantibodies;
4. no typical autoantibodies detected (about 20% of individuals effected by AIH), so called autoantibody negative AIH.

Tests and procedures used to diagnose autoimmune hepatitis include blood tests and liver biopsy. That is, as noted before on a negative basis, blood tests allow to distinguish the hepatitis from viral hepatitis and other disorders with similar symptoms due to the absence on positivity on said other disease, thus excluding said disease.

There are various diagnostic markers described in the art allowing to determine autoimmune hepatitis. However, most of them are not associated with autoimmune hepatitis only. However, anti-ASPGPR (anti-asialoglycoprotein receptor) is reported in few studies with moderate sensitivities between 70 to 76% and high specificities around 95%. (Hausdorf et al, Int. J. Clin. Chem., 2009 408, 19 bis 24) but the assays could not be established as routine diagnostic tool due to difficulties to generate the target molecule ASGPR. ASGPR is a glycosylated heterodimeric receptor with conformational epitopes. In addition, there is no description of anti-ASGPR in pediatric patients.

WO 98/35987 A1 identifies FTCD antigen being liver specific to serve as a diagnostic tool for AIH type II.

U.S. Pat. No. 5,830,667B1 describes human P450 IID6 cytochrome derived peptide fragments, anti-peptide fragments antibodies and applications thereof in the diagnosis between AIH and other chronic viral forms of hepatitis.

US 2003/0232392 A1 disclose composition and method for diagnosing AIH detecting SLA antigens.

The huntingtin interacting protein 1 related protein (HIP1R) was identified by searching databases for homologs of the huntingtin interacting protein (HIP1). The HIP1R seems to be expressed ubiquitously and it represents a component of clathrin coated pits and vesicles that may link the endocytic machinery to the active cytoskeleton. It is assumed that by binding 3-phosphoinositides, it may act through the ENTH domain to promote cell survival by stabilizing receptor tyrosine kinases following ligand induced endocytosis.

There are only very few reports on autoantibodies against HIP1R. For example, Scanlan et al, 2002, Cancer Res, 62 (14) 4041-7 describe a cancer related serological recognition of human colon cancer whereby antigens identified having antibodies in sera from patients reacting with 13 different antigens including HIP1R while sera from normal blood donors do not. However, anti-HIP1R was only detectable in 5/74 (6,8%) of these colorectal cancer patients.

Up to now no specific diagnostic marker has been established for autoimmune hepatitis. Although some literature describes autoantibody test useful for the diagnosis of AIH, said test suffer from low disease specificity (anti-lactoferrin antibodies; ALA) and sensitivity (ANA, SMA, LKM, SLA). The required screening tests for the most relevant autoantibodies are time consuming and demanding. Namely, the most relevant autoimmune antibody tests are based on immunofluorescent study on rodent tissue sections requiring two days for preparation and experience with the staining pattern.

The anti-ASGPR test described so far is not evaluated in the pediatric cohort.

In view of the above, there is an ongoing need for providing a diagnostic tool and a method allowing diagnosis and assessing the risk of development or for the therapy control of autoimmune hepatitis in a subject. In addition, this tool, e.g. a kit, or a method should preferably allow to differentiate between different types of hepatitis, in particular, represents a diagnostic marker for autoimmune hepatitis and allow to differentiate between autoimmune hepatitis and other types of hepatitis.

BRIEF DESCRIPTION OF THE PRESENT INVENTION

The present inventors aimed to provide a method for determining or diagnosing the presence or absence, or the risk of development or for the therapy control of autoimmune hepatitis in a subject comprising analyzing a biological sample provide from said subject for the presence or absence of antibodies against huntingtin interacting protein 1 related protein (HIP1R) or against immunoreactive peptides derived from HIP1R, whereby the presence of antibodies against HIP1R or against immunoreactive peptides derived from HIP1R is indicative for the presence, or the risk of development or for therapy control of autoimmune hepatitis in said subject.

In an embodiment, the antibodies are autoantibodies and the subject is a human.

In another embodiment, the biological samples are a body fluid, preferably, blood in particular serum or plasma.

In a further embodiment, the present invention allows to identify the status of the disease, in particular, the activity of the disease in a subject afflicted with autoimmune hepatitis. Further, the present invention allows to differentiate hepatitis, namely, to differentiate autoimmune hepatitis against other types of hepatitis including virus infection. The method according to the present invention is also useful in pediatric and adult subjects.

In a further embodiment, the present invention relates to the use of a test kit in a method according to the present invention for diagnosing the presence or absence, or for the risk of development, or for the therapy control of autoimmune hepatitis in a subject comprising detecting agents for determining antibodies against HIP1R or against immunoreactive peptides derived from HIP1R, preferably human HIP1R in a biological sample of a subject to be tested and instructions on how to use said test kit.

Further, the present invention relates to the use of HIP1R or an immunoreactive peptide derived from HIP1R in diagnosis, risk assessment or therapy control of hepatitis diseases by determining the presence of (auto)antibodies against HIP1R in said subject.

Finally, the present invention relates to a method of treating autoimmune hepatitis whereby autoimmune hepatitis is diagnosed based on the presence of autoantibodies against HIP1R followed by treating said individual to slow or stop the immune system attack on the liver, e.g. by inducing tolerance or by B-cell depletion.

DETAILED DESCRIPTION OF THE PRESENT INVENTION

Figure 1:
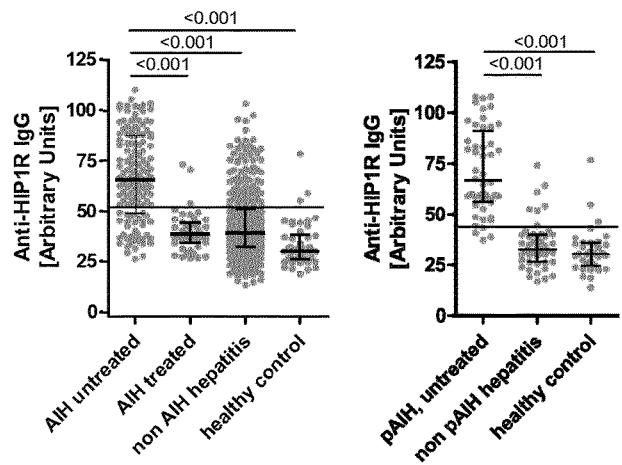
FIG. 1: Arbitrary units of the serum antibody detection in adult (left) and pediatric (right) patients with untreated autoimmune hepatitis (AIH; adults n=86, pediatric AIH pAIH n=48), treated AIH (adults n=34) non AIH liver diseases (adults n=155, pediatric n=51) and healthy control (adults=50, pediatric n=34). Untreated AIH was compared to all other groups with the Kruskal-Wallis test and the Dunn's multiple comparison test as post hoc analysis.

In a first aspect, the present invention relates to a method for determining or diagnosing the presence or absence, or the risk of development or for the therapy control of autoimmune hepatitis in a subject comprising, analyzing a biological sample provided from said subject for the presence or absence of antibodies against human huntingtin interacting protein 1 related protein (HIP1R) or against immunoreactive peptides derived from HIP1R, whereby the presence of antibodies against HIP1R or against immunoreactive peptides derived from HIP1R is indicative for the presence, or the risk of development or for the therapy control of autoimmune hepatitis in said subject.

That is, the present inventors recognized that subjects afflicted with autoimmune hepatitis or having risk of developing autoimmune hepatitis or for the therapy control of autoimmune hepatitis have autoantibodies against the protein huntingtin interacting protein 1 related (HIP1R).

The HIP1R is expressed ubiquitously in the body. The present inventors demonstrate that HIP1R represents an entity to which autoantibodies can be found in subject afflicted with autoimmune hepatitis (either unknown AIH or diagnosed AIH). Hence, determining the presence of antibodies, in particular, human autoantibodies, against HIP1R is indicative of the presence or the risk of development, or for the therapy control of autoimmune hepatitis in a subject.

Until today autoimmune hepatitis can be diagnosed by expensive and cost intensive diagnosis or exclusion of other diseases, disorders or conditions only. In contrast, it is now possible to diagnose the presence or the risk of development of autoimmune hepatitis or for the therapy control of autoimmune hepatitis in a subject with a simple test system or test kit based on the method described herein.

As demonstrated in the examples, the determination of antibodies against HIP1R allows identifying individuals suffering from AIH.

For example, the present invention allows to identify the therapy regimen of an individual in need thereof. That is, identifying the presence of autoantibodies against HIP1R pin points to a therapy comprising B-cell depletion or inducing tolerance in T-cells or to any other therapy in order to eliminate HIP1R specific antibodies.

At present the goal of treatment is to slow or stop the immune system attack on the liver. Hence, the treatment and medications are based on lowering immune system activity. Initially, prednisone is generally used, as a second medication, azathioprine may be recommended in addition to prednisone.

However, a main problem are the side effects known for prednisone, in particular, when administered over a long time. The treatment regimen of autoimmune disease however requires that the people need to continue take the prednisone for at least 18 to 24 months and may remain at for life, thus, the side effects including diabetes, osteoporosis as well as osteonecrosis, high blood pressure, glaucoma and weight gain occur with high incidence. In case of cirrhosis, a liver transplantation is required. Thus, it is important to identify and determine autoimmune hepatitis at the earliest to avoid e.g. liver transplantation in view of cirrhosis.

The terms "patient" and "subject" and "individual" are used herein interchangeably and refers to patients, subjects or individuals of humans or other mammals and includes any individual it is desired to examine or treat using the methods of the invention. However, it will be understood that "patient" does not imply that symptoms are present.

As used herein, the terms "comprising", "comprises" and "comprised of" are synonymous with "including", "includes" or "containing", "contains", and are inclusive or open ended and do not exclude additional, non-recited members, elements or method steps. It will be appreciated that the terms "comprising", "comprises" and "comprised of" as well as "including", "includes", or "containing", "contains" as used herein comprise the terms "consisting of", "consists" and "consist of".

All references cited in the present specification are hereby incorporated by reference in their entirety. In particular, the teachings of all references herein specifically referred to are incorporated by reference.

With the term "providing" is meant that the sample provided as an isolated sample originating from the subject.

With the term "obtain from" is meant that a sample, such as for example serum has been isolated from or derived from a particular source of the subject. For example, the sample can be obtained from tissue or a body fluid isolated directly from the subject. For clarification, the term "obtained from" does not include the surgical step itself but relates to an isolated sample.

As used herein, the terms "a", "an" and "the" mean "one or more" when used in this application, including the claims. Unless defined otherwise, all technical scientific terms used herein have the same meaning as commonly understood one of the ordinary skilled in the art to which the present disclosed subject matter belongs.

The terms "diagnosing" and "diagnosis" as used herein refers to method by which a skilled person can estimate an even determine whether or not a subject is suffering from a given disease, disorder or condition. The skilled artisan makes the diagnosis on the basis of one or more diagnostic indicators, namely antibodies, the amount (including presence or absence) of which is an indicator for the presence severity, or absence of the condition.

Along with diagnosis, therapy control and clinical prognosis is also an area of great concern and interest. It is important to know the severity of the diseases as well as the activity of the diseases in order to design the most effective therapy. Hence, "making a diagnosis" or "diagnosing", as used herein, may further include making a prognosis which can provide from predicting a clinical outcome, selecting an appropriate treatment, or monitoring a current treatment and potentially change in the treatment based on the measure of diagnostic antibodies, in particular, autoantibodies.

The term "determining" or "analyzing" as used herein refers to assessing the presence, absence, quantity, level or amount of the respective (auto)antibodies within the subject derived sample, including qualitative or quantitative concentration levels of said substances otherwise evaluating the values or categorization for a subject clinical parameter.

The term "biological sample" as used herein refers to a sample that may be extracted, untreated, treated, isolated or concentrated from a patient. Suitably, the biological sample is selected from any part of the patient's body, including but not limited to hair, skin, nails, tissues or body fluids, such as saliva, synovia and blood. It is preferred that the samples are from the blood of said individual, like from the sera.

Throughout this specification, unless the content requires otherwise, the word "comprise" will be understood to apply the conclusion of a stated stable element or group of steps or elements but not the exclusion of any other step or element or group of steps or elements.

That is, in an embodiment of the present invention the biological sample is a body fluid, preferably blood, in particular, serum. The skilled person is well aware of the suitable steps to obtain suitable biological samples for analyzing the same in the absence or presence of antibodies against HIP1R.

As mentioned, the inventors recognized that antibody production against HIP1R can be correlated with the presence of autoimmune hepatitis.

The term "presence of antibodies against HIP1R or against immunoreactive peptides derived from HIP1R" include the level or amount of antibodies against HIP1R in the sample over a specific threshold whereby said threshold is e.g. representative of normal blood donors representing subjects not afflicted with autoimmune hepatitis.

In an embodiment of the present invention, multiple determinations of the antibodies over time can be made to facilitate stratification, diagnosis and/or prognosis.

As used herein, the term immunoreactive peptide derived from HIP1R refers to polypeptides or oligopeptides derived from the HIP1R protein. These immunoreactive fragments contain the epitope of the (auto)antibodies to be determined. For example, an immunoreactive peptide according to the present invention is a peptide derived from the human HIP1R protein of SEQ ID No. 1. In an embodiment of the present invention, the immunoreactive peptide is the peptide of SEQ ID No. 2.

In some embodiments of the methods disclosed herein, detecting, determining or analyzing the presence of the (auto)antibodies in the sample can include binding the (auto)antibodies to an antigen and then detecting either the binding event or the presence of the (auto)antibody isolated from the biological sample. Suitable methods and techniques for detecting the (auto)antibodies include, but are not limited to enzyme-linked immunosorbent assay (ELISA), radioimmunoassay (RIA), multiplex immunoassay or immunofluorescence assay, western blot, line assay or dot blot and other immunoprecipitation and immunoblotting techniques. For example, suitable arrays may be used for immunodetection.

The skilled person is well aware of useful immunodetection methods allowing analyzing the same for the presence or absence of antibodies against HIP1R. For example, the biological sample obtained from the subject is contacted with an antigen, namely with the HIP1R oligo- or polypeptide or the full protein containing the (auto)antibody immunoreactive peptide with the epitope of the (auto)antibody, thus, allowing binding of the (auto)antibody to said peptide. In this connection, the term "polypeptide" or "protein" which are used interchangeably herein, refers to a polymer of amino acid having a length of at least 50 aa. The term "oligopeptide" refers to a polymer of amino acids having a length of from 5 to 49 aa.

The method according to the present invention generally relates to contacting the chosen biological sample with the antigen under conditions effective and for a period of time sufficient to allow the formation of immune complexes formed by the (auto)antibody and the antigen. Said antigen antibody mixture can be detected by known means and methods. That is, detection of immune complex formation of antigen/(auto)antibody can be achieved through the application of numerous approaches. These methods are generally based upon the detection of a label or marker, such as any radioactive, fluorescence, biological or enzymatic tags or labels of standard use in the art. Of course, one may find additional advantageous through the use of a secondary binding ligand such as a second antibody or a biotin/avidin (streptavidin) ligand binding arrangement as it is known in the art. Typically, the method according to the present invention is a method where the detection is performed using an immunoassay, preferably with direct or indirect coupling of one reactant to a detectable marker substance.

In some embodiments, the primary immune complex can be detected by a second binding ligand that has binding affinity for the antigen or the (auto)antibody present in the sample, for example reactivity to the Fc region of the (auto)antibodies or having reactivity to a region of the antigen different to the binding region of the (auto)antibody. In these cases, the second binding ligand can be linked to a detectable label or marker molecule. The second binding ligand is itself often an antibody which may thus be termed a secondary antibody. Typically, the primary immune complexes are contacted with the labelled secondary binding ligand or antibody under conditions effective and for a period of time sufficient to allow the formulation of secondary immune complexes. The secondary immune complexes are then generally washed to remove of any can bound labelled secondary antibodies or ligands, and the remaining label in the secondary immune complex is then detected.

The second binding ligand, such as an antibody, having binding activity for either the antigen or (auto)antibody, may also be used to bind to the primary immune complexes. The second binding ligand may contain an enzyme capable of processing a substituted detectable to a product, and, hence amplify a signal over time. Alternatively, comparative immunodetection may be used. The skilled person is well aware of suitable methods.

It is preferred that the biological sample from the subject, preferably, a human subject is selected from blood, tissue or fluid, preferably selected from hair, skin, nails, saliva, synovia, liquid and blood, in particular, serum or plasma derived from blood.

The (auto)antibodies to be detected may be of the IgA and/or IgG type. In an embodiment, IgG type antibodies are detected. Although it is sufficient to detect one type of antibodies, either IgA or IgG (auto)antibodies, in an embodiment of the present invention both IgA and IgG (auto) antibodies against HIP1R are detected.

In a particular preferred embodiment, the subject is a human and the autoantibodies are human autoantibodies.

In an embodiment of the present invention, the method allows to identify the status of the disease, in particular, the activity of the disease in a subject afflicted with autoimmune hepatitis.

That is, based on the status of the subject, the level or amount of the (auto)antibodies against HIP1R can be detected. While untreated AIH patients have a high level or amount of HIP1R (auto)antibodies, the level or amount is lower thus, demonstrating an effective treatment. Thus, determining quantitatively or semi-quantitatively the amount of (auto)antibodies against HIP1R allows to determine the treatment status and the treatment success in an individual diagnosed with AIH. Namely, it is possible to use the method for the therapy control of AIH by determining the status of the subject under treatment.

Further, the present invention allows to diagnose even patients with untreated AIH and normal immunoglobulin G levels determining anti-HIP1R antibodies. In addition, anti-HIP1R concentrations are correlated generally with serological activities of untreated AIH patients.

In an aspect of the present invention, the method allows to differentiate autoimmune hepatitis against other hepatitic diseases including infectious hepatitis, metabolic induce hepatitis, non-alcoholic fatty liver disease and hepatitis virus infections, in particular, hepatitis virus infection A, B, C, D, and/or E and cholestatic liver diseases, in particular primary sclerosing cholangitis and primary biliary cholangitis.

In an embodiment of the present invention, the method is for use in pediatric subjects. That is, the autoimmune hepatitis can be diagnosed and detected using the method according to the present invention.

That is, the method according to the present invention allows for the first time the diagnosis of the pediatric group in mammals, in particular, humans.

In a further aspect, the disclosed subject matter provides test kits or diagnostic kits for use in a method according to the present invention. In particular, immunological kits for use in detecting (auto)antibodies in biological samples allow diagnosis of autoimmune hepatitis. That is, the present invention provides a test kit for use in a method according to the present invention for diagnosing or determining the presence, or the risk of a development as well as for the therapy control of autoimmune hepatitis in a subject comprising detecting agents for determining antibodies against HIP1R or against immunoreactive peptides derived from HIP1R, preferably human HIP1R, in a biological sample of a subject to be tested and instructions on how to use said test kit.

In an embodiment of the test kit is an ELISA, RIA, multiplex immunoassay or immunofluorescence assay, western blot, line assay or dot blot assay.

The skilled person is well aware of suitable kits in form of test kits or diagnostic kits.

The kits can generally comprise one or more antigens, namely oligo- or polypeptides of HIP1R that can immune react with the (auto)antibodies. Typically, the immunodetection kits will comprise in suitable container (s), one or more antibody immunoreactive peptide antigens derived from HIP1R. Said antigens useful in the presently claimed methods and test kits may be the full HIP1R or immunoreactive peptides derived therefrom. For example, the antigen may be a polypeptide or oligopeptide derived from SEQ ID No. 1 (human HIP1R).

In certain embodiments, the antigen can be provided bound to a solid support, such as for example a column matrix or a well of a microtiter plate, a membrane, beads, dips sticks or the like. The solid support may be in form of an array. Alternatively, the support can be provided as a separate element of the kit.

In an embodiment of the present invention, the use of a kit allows to diagnose, assess the risk or to control therapy hepatitis diseases by determining the presence of (auto) antibodies ZHIP1R. In a further embodiment, the use of a test kit or diagnostic kit according to the present invention allows for differential diagnosis of hepatitis, in particular for differential diagnosis of autoimmune hepatitis.

The test kit for use according to the present invention includes beside the antigen a detection agent for the antibodies which may be an antibody, antibody fragment etc. In addition, the kit may comprise more than one detection agents. If required, the kit further comprises substrate and further means for allowing reaction with an enzyme used as a label for the detecting agent which may be an antibody.

The immunodetecting agent of the kit can include detectable labels that are associated with or linked to the given detecting agent, in particular, the detecting antibody. Detectable labels that are associated with or attached to a secondary binding ligand are also contemplated. Detectable labels include dyes, illuminescent or fluorescent molecules, biotin, radiolabels or enzymes. Typical examples for suitable labels include commonly known fluorescent molecules, like rhodamine, fluorescein, green fluorescent protein or luciferase, or alkaline phosphatase and horseradish peroxidase as examples for suitable enzymes.

Optionally, the kits further comprise positive and negative controls for verifying the results obtained when using the kit. The components of the kits can be packaged either in aqueous medium or lyophilized form and, in addition, the kit comprise one or more containers allowing to conduct the detection. In addition, the test kit comprises instructions for use of the kit.

Moreover, the present invention relates to the use of HIP1R or an immunoreactive peptide derived from HIP1R, in the diagnosis of the presence or absence of autoimmune hepatitis diseases in an individual, in particular in an individual supposed to be afflicted with hepatitis, by determining the presence or absence of (auto)antibodies against HIP1R. In another embodiment, the present invention relates to the use of HIP1R or an immunoreactive peptide derived from HIP1R in the therapy control of AIH in an individual afflicted with AIH by determining the presence or absence of (auto) antibodies against HIP1R. In an embodiment, the use is in vitro.

In particular, the present invention refers to the use of HIP1R or an immunoreactive peptide derived from HIP1R for differential diagnosis of hepatitis, in particular, for differential diagnosis for autoimmune hepatitis or exclusion of autoimmune hepatitis. That is, it is described for the first time that a positive diagnostic is provided allowing positive assessment of autoimmune hepatitis.

Moreover, the present invention relates to the use of peptides derived from HIP1R namely immunoreactive peptides including the full protein in prophylaxis and/or treatment of autoimmune hepatitis. It has been shown that use of peptides derived from the antigen of said (auto)antibodies are suitable in the treatment of said autoimmune disease. That is, the use of HIP1R including the immunoreactive peptides of said molecules allow to induce tolerance, thus, being useful in prophylaxis and therapy of autoimmune hepatitis. For example, HIP1R or an immunoreactive peptide derived from HIP1R may be used for systemic or local therapy of diseases, disorders or conditions which are associated with an immunoreaction against said compound. The administration thereof may be effected orally, parenterally or via mucosal membranes. For example, the HIP1R or an immunoreactive peptide derived therefrom may be used to either induce a tolerance of the immune system or to eliminate T-cells and B-cells reacting therewith. Thus, in an embodiment, the present invention identifies a method of prophylactic or therapeutic treatment of subjects suffering from autoimmune hepatitis including administering HIP1R or immunoreactive fragments thereof for B-cell elimination or T-cell tolerance reduction to the subject suffering therefrom. Alternatively, the reactive B-cells or T-cells may be depleted in vitro by known means, for example, by blood purification or by dialysis, using an immunoreactive peptide or the full protein of HIP1R.

Further, the method according to the present invention is suitable for determining the therapy regimen. It has been recognized that after treatment of autoimmune hepatitis, the level or amount of the (auto)antibodies against HIP1R is reduced. Thus, this marker represents a suitable readout system for determining success of therapy, in particular, on the humoral immune response.

Finally, the present invention provides pharmaceutical compositions containing HIP1R molecules including immunoreactive peptides for use in the prophylaxis and treatment of the autoimmune hepatitis. The pharmaceutical composition may be provided in a suitable form. The skilled person is well aware of useful forms, dosages etc.

EXAMPLES

The following examples have been included to illustrate modes of the present disclosed subject matter. In light of the present disclosure and the general level of the skilled in the art, those skilled will appreciate that the following examples are intended to be exemplary only and that numerous changes, modifications and alterations can be applied without deporting from the scope of the present disclosed subject matter.

The present invention allows to improve the current autoantibody test for the conformation or exclusion of AIH, namely: the method and kits according to the present invention have a better sensitivity and/or specificity to diagnose AIH compared to the routine testing for ANA, SMA, LKM, SLA. Further, the requirement for time and experience of the technician for the autoantibody tests are reduced compared to the routine approach with immunofluorescence. The antigen represents a robust target antigen for the autoantibody test for example compared to the ASGPR molecule. In addition, the test is suitable for all age groups.

The target antigen can be synthesized easily as recombinant peptide/protein and represents a stable antigen. To conclude, the method and test according to the present invention are superior with respect to time sensitivity and specificity as well as suitability for different age groups compared to the long tests described so far.

Example 1

In ten patients with untreated AIH and control patients with a viral hepatitis a screen for immunoglobulin autoantibodies were performed on a protein macro array. One of the autoantigens mostly recognized is a HIP1R fragment. The additional examples are continued with the HIP1R fragment of SEQ ID No. 2, namely MGQLQDQQ ALRHMQASLVRTPLQGILQLGQELKPKSLDVRQE:

Example 2: ELISA Test with Immunoreactive Peptide of HIP1R Fragment

For performing the ELISA test, 96 well plates (Maxisorb, Nunc, Denmark) were coated with 0.01 µg of HIP1R fragment of SEQ ID No. 2 per well in 5% bovine serum albumin solution in Tris buffer saline (TBS) overnight at 4° C. Then the plates were blocked with 300 µm TBS in 5% bovine serum albumin (BSA) per well for 30 minutes at room temperature. The plates were incubated with 100 µl diluted sera or plasma (1:100) and TBS for 30 minutes at room temperature. After 30 minutes of incubation, the plates were washed three times with 300 µl TBS with 0.025% Tween™ Twenty (TBST; nonionic detergent). Next 100 µl of a secondary peroxidase-rabbit anti-human IgG labelled with horseradish peroxidase (Jackson Immunoresearch Europe Ltd, Newmarket UK) was added in a dilution of 1:10.000 in TBST. The plates were incubated for 30 minutes at room temperature and washed three times with TBST. The color reaction was performed with 3.3', 5.5' tetramethyl benzydine (biolend, San Diego, California, USA) for up to 30 minutes according to the manufacturer's instructions and the optical density (OD) were read at 450 nm in an ELISA reader. Thereby serum or plasma of five patients with a high/medium-high/medium/medium-low/low OD was used. The concentration of IgG antibodies against HIP1R in this serum was defined as 100/80/60/40/20 arbitrary units.

Example 3

Serum samples of patients with biopsy proven AIH, non-AIH liver disease and healthy adult controls (blood donors and employees of the Hanover Medical School) and pediatric control without elements of a liver or autoimmune disease have been tested with the semi-quantitative ELISA described in example 2.

As shown in FIG. 1 using arbitrary units of the serum antibody detection in adult (serum and plasma samples pooled) and pediatric patients (serum samples), an untreated autoimmune hepatitis the level of autoantibodies against HIP1R is significantly increased. This is particularly true for the pediatric group, see FIG. 1 on the right. The black horizontal line represents the cut-off level for the distinction of untreated AIH versus non-AIH liver disease. This cut-off level was determined with the receiver-operating-characteristic curve and the Youden's index. Due to different antiHIP1R levels of non-AIH patients in children and adults, age dependent cut-off levels were used.

In FIG. 2, the adult and pediatric patient cohorts have been split further with respect to the different type of non-AIH liver disease. That is, the following pediatric patient cohort has been tested:

Pediatric patient cohort (latest retrospective data set with serum samples):

| | |
|---|---|
| Untreated pediatric AIH (pAIH): | n = 47 |
| Non-AIH liver disease: | |
| Autoimmune sclerosing cholangitis (ASC)/pAIH-PSC: | n = 9 |
| Primary sclerosing cholangitis (PSC): | n = 19 |
| Toxic hepatitis: | n = 2 |
| Non-alcoholic fatty liver disease (NAFLD): | n = 14 |
| Cryptogenic hepatopathy: | n = 4 |
| Alpha-1-Antitrypsin deficiency (A1AT): | n = 34 |
| Healthy control: | n = 34 |

Figure 2A:
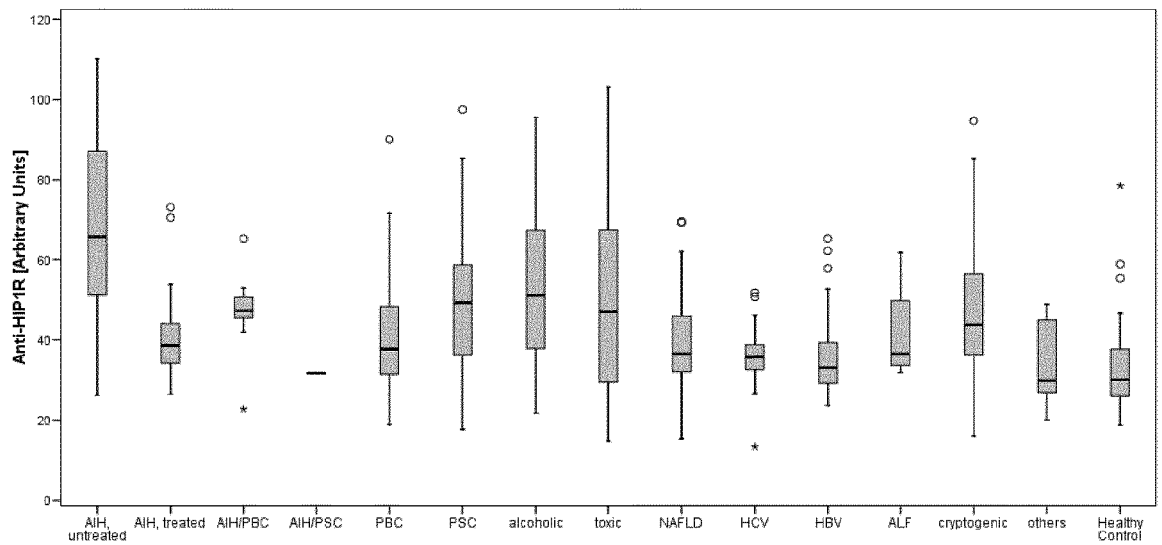
FIG. 2: Shown are the results of the adult patient cohort (FIG. 2a) and the pediatric patient cohort (FIG. 2b).
Figure 2B:
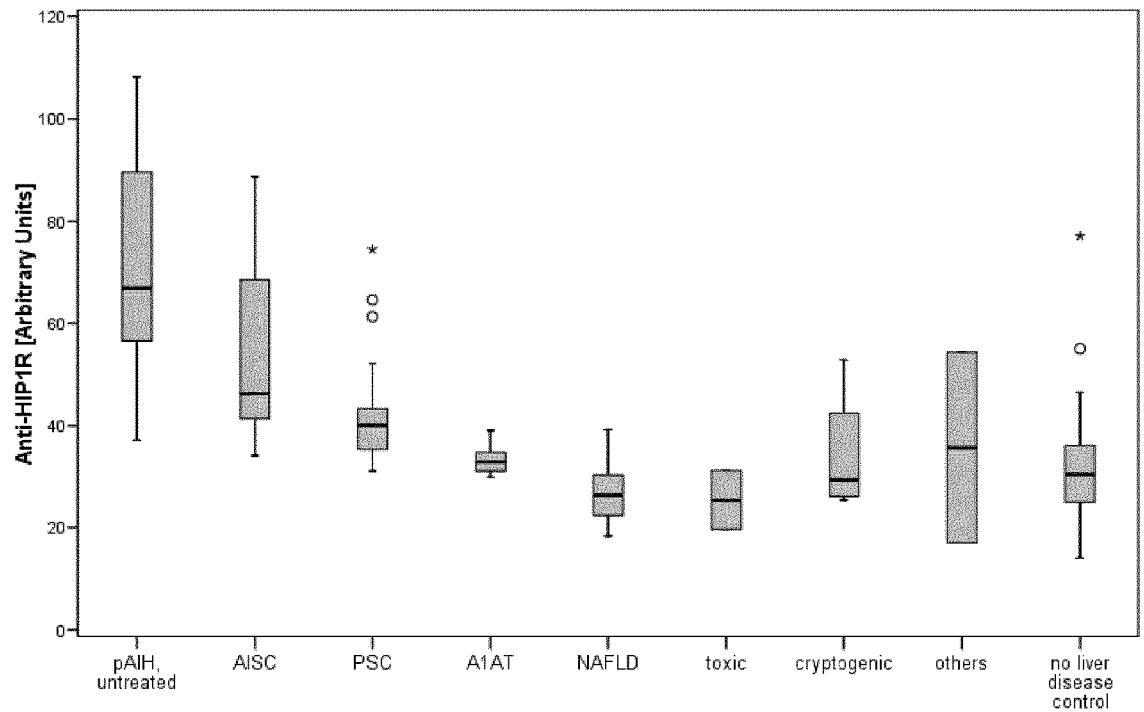

Adult patient cohort (combined data set from retrospective serum and prospective plasma samples):

| | |
|---|---|
| Untreated AIH: | n = 139 |
| Treated AIH: | n = 44 |
| AIH/PBC: | n = 12 |
| AIH/PSC: | n = 1 |
| PBC: | n = 44 |
| PSC: | n = 44 |
| Alcoholic hepatitis: | n = 35 |
| Toxic hepatitis: | n = 20 |
| NAFLD: | n = 59 |
| Hepatitis C virus infection (HCV): | n = 31 |
| Hepatitis B virus infection (HBV): | n = 33 |
| Acute liver failure (ALF): | n = 4 |
| Cryptogenic hepatopathy: | n = 69 |
| Other liver diseases: | n = 11 |
| Healthy controls: | n = 46 | n FIG. 2 the results are shown demonstrating that in the cohort of untreated adult (FIG. 2a)= and pediatric AIH (FIG. 2b) the level of anit-HIP1R autoantibodies is highest. Of note, in case if patients have an autoantibody negative AIH, that is being completely negative for ANA, SMA, LKM-1, and SLA, five out of six patients (adults) have anti-HIP1R above the cut of, thus, being diagnosed for AIH.

Regarding the healthy controls, two out of 34 children demonstrated an anti-HIP1R value above the cut of while in adults three out of 46 showed the same result. It is described in literature, see Scanlan et al, above, that five out of 74 in the adult colon cancer cohort demonstrated autoantibodies against HIP1R.

In table 1 a comparison of anti-HIP1R versus local routine autoantibody diagnostics in adult and pediatric cohorts are shown.

TABLE 1

Comparison of anti-HIP1R vs. local routine autoantibody diagnostic (immunofluorescence on rodent tissue for ANA, SMA, LKM; Elisa for SLA):

| | | | Sample number | AUC | 95% Confidence Interval (CI) | Cut off | Odds ratio | CI | Sensitivity | CI |
|---|---|---|---|---|---|---|---|---|---|---|
| Adults | Serum (retrospective training cohort) | anti-HIP1R | 251 | 0.860 | 0.814-0.907 | >52.66 Arbitrary Units | 12.78 | 6.91-23.66 | 0.766 | 0.665-0.845 |
| | | ANA | 248 | 0.767 | 0.708-0.826 | ≥1:80 | 8.15 | 4.39-15.16 | 0.819 | 0.723-0.888 |
| | | SMA | 247 | 0.545 | 0.467-0.624 | ≥1:80 | 1.53 | 0.91-2.58 | 0.473*** | 0.370-0.579 |
| | | LKM | 244 | 0.522 | 0.450-0.594 | ≥1:40 | not applicable | | 0.043*** | 0.014-0.114 |
| | | SLA | 231 | 0.513 | 0.438-0.587 | >40% binding | 5.31 | 0.54-51.83 | 0.035*** | 0.009-0.107 |
| | Plasma (prospective validation cohort) | anti-HIP1R | 238 | 0.761 | 0.685-0.837 | >52.66 Arbitrary Units | 7.23 | 3.52-14.88 | 0.711 | 0.555-0.832 |
| | | ANA | 231 | 0.762 | 0.686-0.837 | ≥1:80 | 7.89 | 3.19-19.54 | 0.867 | 0.725-0.945 |
| | | SMA | 228 | 0.716 | 0.626-0.806 | ≥1:80 | 3.10 | 1.45-6.64 | 0.778 | 0.625-0.883 |
| | | LKM | 226 | 0.524 | 0.429-0.620 | ≥1:40 | 4.24 | 0.83-21.74 | 0.067*** | 0.017-0.193 |
| | | SLA | 175 | 0.519 | 0.419-0.619 | >40% binding | 6.19 | 0.55-70.00 | 0.045*** | 0.008-0.167 |
| Children | Serum (retrospective training cohort) | anti-HIP1R | 96 | 0.946 | 0.904-0.988 | 43.28 Arbitrary Units | 87.86 | 21.30-362.44 | 0.938 | 0.818-0.984 |
| | | ANA | 102 | 0.826 | 0.743-0.909 | age dependent | 24.60 | 8.12-74.50 | 0.745* | 0.607-0.849 |
| | | SMA | 100 | 0.792 | 0.702-0.882 | age dependent | 7.57 | 3.02-18.96 | 0.648*** | 0.506-0.770 |
| | | SLA | 85 | 0.542 | 0.419-0.665 | >40% binding | not applicable | | 0.083*** | 0.027-0.209 |
| | | LKM | 98 | 0.547 | 0.433-0.661 | ≥1:40 | not applicable | | 0.094*** | 0.035-0.214 |

| Specificity | CI | Positive predictive value | CI | Negative predictive value | CI | Accuracy | CI | |
|---|---|---|---|---|---|---|---|---|
| 0.796 | 0.722-0.854 | 0.692 | 0.593-0.777 | 0.850 | 0.780-0.902 | 0.785 | 0.728-0.833 | |
| 0.643** | 0.561-0.717 | 0.583 | 0.494-0.667 | 0.853 | 0.773-0.910 | 0.710 # | 0.648-0.765 | # p = 0.063 |
| 0.630** | 0.548-0.705 | 0.436*** | 0.338-0.538 | 0.664*** | 0.581-0.739 | 0.571*** | 0.506-0.633 | |
| 1.000*** | 0.969-1.000 | 1.000 | 0.396-1.000 | 0.633*** | 0.569-0.694 | 0.639*** | 0.575-0.699 | |
| 0.993*** | 0.957-1.000 | 0.750 | 0.219-0.987 | 0.639*** | 0.572-0.701 | 0.641*** | 0.575-0.702 | |
| 0.746 | 0.678-0.805 | 0.395 | 0.290-0.510 | 0.917 | 0.860-0.953 | 0.739 | 0.678-0.793 | |
| 0.548*** | 0.474-0.621 | 0.317 | 0.238-0.408 | 0.944 | 0.878-0.977 | 0.610** | 0.544-0.673 | |
| 0.470*** | 0.396-0.545 | 0.265 # | 0.194-0.350 | 0.896 | 0.813-0.946 | 0.530*** | 0.464-0.597 | # p = 0.0502 |
| 0.983*** | 0.948-0.996 | 0.500 | 0.139-0.861 | 0.809** | 0.750-0.858 | 0.801 | 0.742-0.850 | |
| 0.992*** | 0.952-1.000 | 0.667 | 0.125-0.982 | 0.756*** | 0.683-0.817 | 0.754 | 0.682-0.815 | |
| 0.854 | 0.716-0.935 | 0.865 | 0.736-0.940 | 0.932 | 0.803-0.982 | 0.896 | 0.813-0.946 | |
| 0.894 | 0.761-0.960 | 0.891 | 0.756-0.959 | 0.750* | 0.614-0.852 | 0.814 | 0.722-0.881 | |
| 0.804 | 0.656-0.901 | 0.795 | 0.642-0.897 | 0.661* | 0.521-0.778 | 0.720** | 0.620-0.803 | |
| 1.000* | 0.883-1.000 | 1.000 | 0.396-1.000 | 0.457*** | 0.347-0.571 | 0.482*** | 0.374-0.593 | |
| 1.000* | 0.902-1.000 | 1.000 | 0.463-1.000 | 0.484*** | 0.380-0.589 | 0.510*** | 0.408-0.612 | |

Fisher's exact test (AIH vs non-AIH) for Sensitivity, Specificity, Positive predictive value, Negative predictive value and Accuracy ((true positive + true negative)/total number):
*p < 0.05;
**p < 0.01;
***p < 0.001; not significant p values are not depicted;
# indicate trend to significant results
Conclusion:
White fonts on dark grey ground indicate significant superiority of HIP1R
Dark grey fonts on light grey ground indicate significant inferiority of HIP1R
"#" indicate trend to superiority of HIP1R In addition, a correlation with disease severity has been conducted. Namely, a correlation analysis with the Spearman rank correlation coefficient (SR) with markers of AIH disease activity (Immunoglobulin G (n=172); alanine aminotransferase (ALT; n=178); aspartate aminotransferase (AST; n=178) in adult and pediatric AIH (n=94 and 47) patients before and under therapy (only adults; n=38). **p<0.01, see FIG. 3.

Figure 3:
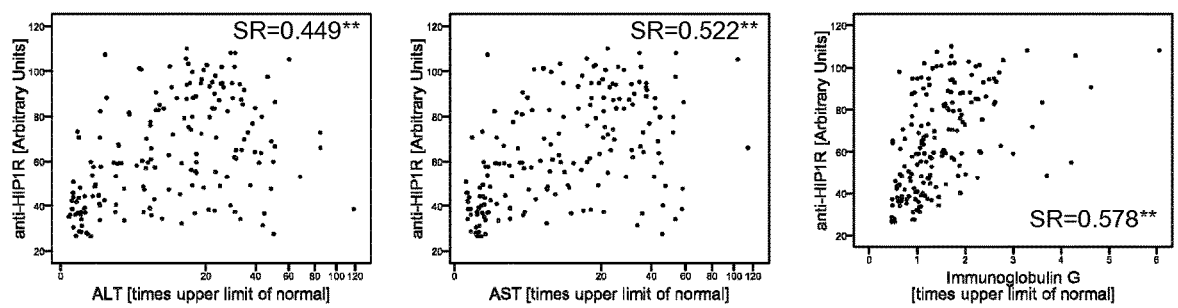
FIG. 3: Correlation analysis with the Spearman rank correlation coefficient (SR) with markers of AIH disease activity (immunoglobulin G (n=172); alanine aminotransferase (ALT; n=178), Aspartate aminotransferase AST; n=178) in adult and pediatric AIH (n=94 and 47 patients before and under therapy (onl adults; n=38). **p<0.01
Figure 4:
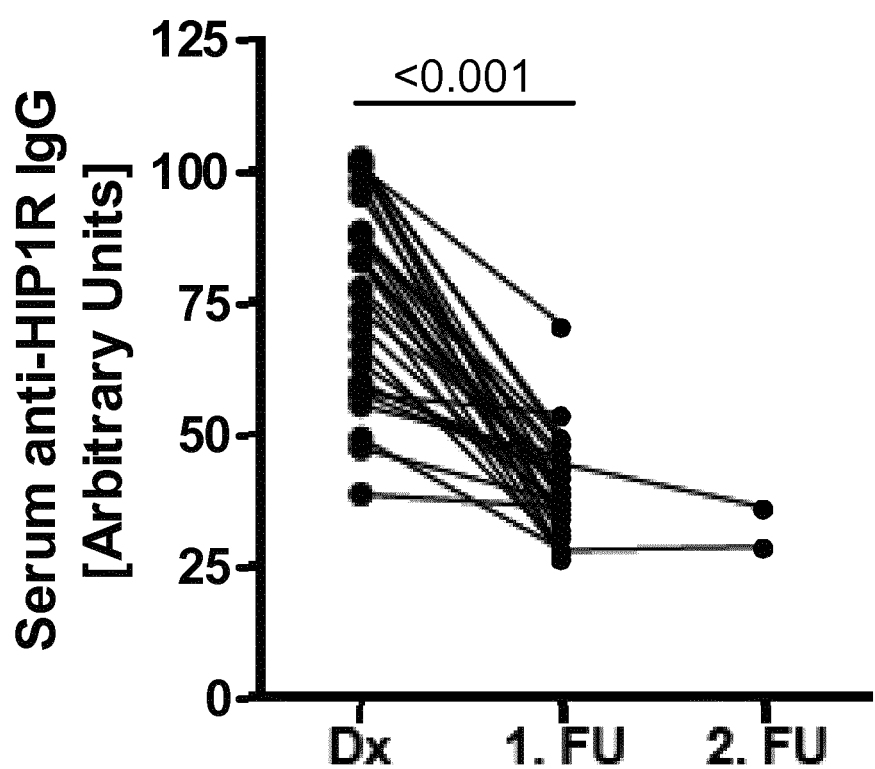
FIG. 4: Anti-HIP1R levels in paired blood samples (n=31) at diagnosis (Dx) and in follow-up (FU) under therapy. Comparison with Wilcoxon matched pairs test.

As demonstrated in FIG. 4 3 longitudinal cohorts under therapy are shown. AntiHIP1R levels in paired blood samples (n=31) at diagnosis (DX) and in follow up (FU: 1. FU after in median 10.5 months (range: 2-93 months) after Dx; 2. FU 12 and 13 months after Dx) under therapy (majority of patients with combination therapy of prednisolone and azathioprine, the others with prednisolone monotherapy) Taken together, the sensitivity of anti-HIP1R exceeds the currently most prevalently used ANA and SMA diagnostics. At the same time, the test provides a very high specificity of 80 and 98% in adult and pediatric patients, respectively. In addition, the method is less time consuming and less operator dependent than currently used ANA/SMA diagnostics. The HIP1R antigen is (as most AIH autoantibodies) non-specifically expressed in the liver. In fact, it is ubiquitously expressed throughout the body. So HIP1R is not liver, but liver disease specific. Thus, it represents a valuable and simple tool to diagnose patients with suspected AIH.

Although anti-HIP1R concentrations are correlated with serological activity of untreated AIH (immunoglobulin G, aminotransferases), even patients with untreated AIH and normal immunoglobulin G levels had diagnostic anti-HIP1R antibodies in approximately 70%.

| | Immunglobulin G | | |
|---|---|---|---|
| | normal | 1-2x elevation | 2x elevation |
| anti-HIP1R negative | 31% | 23% | 13% |
| anti-HIP1R positive | 69% | 77% | 87% |

This underlines that anti-HIP1R antibody status is a marker for untreated AIH independent from the commonly found polyclonal hypergammaglobulinemia.

The invention claimed is:

1. A method for treating autoimmune hepatitis in a human subject, comprising:
   detecting in a blood sample of said human autoantibodies against huntingtin interacting protein 1 related protein (HIP1R) or against immunoreactive peptides derived from HIP1R, wherein a level of said autoantibodies is increased as compared to a healthy control; and
   administering to the human a medication for autoimmune hepatitis.

2. The method of claim 1 wherein the treatment includes the administration of one or more HIP1R immunoreactive peptides.

3. The method of claim 1 wherein the treatment includes the administration of one or more of prednisone and azathioprine.

4. The method of claim 1, wherein the human is an adult human.

5. The method of claim 1, wherein the human is a pediatric human.

6. The method of claim 1, wherein the sample is serum or plasma.

7. The method according to claim 1, wherein said detecting step includes detecting one or more of IgG antibodies and IgA antibodies.

8. The method according to claim 1, wherein the detecting step includes performing an immunoassay.

9. The method according to claim 8 wherein the immunoassay is selected from the group consisting of an ELISA, RIA, multiplex immunoassay, immunofluorescence assay, western blot, line assay, and dot blot assay.

10. The method according to claim 8 wherein the immunoassay includes direct or indirect coupling of one reactant to a detectable marker substance.

* * * * *